United States Patent
Pope et al.

(10) Patent No.: US 11,439,581 B2
(45) Date of Patent: *Sep. 13, 2022

(54) EPILATORY COMPOSITIONS

(71) Applicant: RECKITT BENCKISER HEALTH LIMITED, Slough (GB)

(72) Inventors: Alice Heather Pope, Hull (GB); Terry Alan Cass, Hull (GB); Victoria Mary Morris-Curtis, Hull (GB)

(73) Assignee: Reckitt Benckiser Health Limited, Slough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/075,882

(22) Filed: Oct. 21, 2020

(65) Prior Publication Data

US 2021/0030658 A1 Feb. 4, 2021

Related U.S. Application Data

(63) Continuation of application No. 15/558,764, filed as application No. PCT/GB2016/050793 on Mar. 22, 2016, now abandoned.

(30) Foreign Application Priority Data

Mar. 23, 2015 (GB) ...................................... 1504850

(51) Int. Cl.
| | | |
|---|---|---|
| *A61Q 9/00* | (2006.01) | |
| *A61K 8/92* | (2006.01) | |
| *A61K 8/81* | (2006.01) | |
| *A61K 8/31* | (2006.01) | |
| *A61Q 9/04* | (2006.01) | |
| *A61K 8/29* | (2006.01) | |

(52) U.S. Cl.
CPC .............. *A61K 8/8117* (2013.01); *A61K 8/29* (2013.01); *A61K 8/31* (2013.01); *A61K 8/8111* (2013.01); *A61K 8/922* (2013.01); *A61Q 9/04* (2013.01)

(58) Field of Classification Search
None
See application file for complete search history.

(56) References Cited

U.S. PATENT DOCUMENTS

| | | |
|---|---|---|
| 4,282,877 A | 8/1981 | Mathews |
| 8,038,723 B2 | 10/2011 | Ellis |
| 2004/0175340 A1 | 9/2004 | Gupta |
| 2004/0219118 A1 | 11/2004 | Slavtcheff |
| 2008/0118457 A1 | 5/2008 | Acher |
| 2010/0021411 A1 | 1/2010 | Bosch et al. |
| 2013/0042421 A1 | 2/2013 | Smith |
| 2013/0046256 A1 | 2/2013 | Smith |

FOREIGN PATENT DOCUMENTS

| | | |
|---|---|---|
| GB | 2446576 A | 8/2008 |
| GB | 2501536 A | 10/2013 |
| WO | 2005112876 A1 | 12/2005 |
| WO | 2014198985 A1 | 12/2014 |

OTHER PUBLICATIONS

Definition of "epilation" from dictionary.com, Apr. 5, 2019.
International Search Report and Written Opinion issued in International Application No. PCT/GB2016/050793 dated May 24, 2016.
Combined Search and Examination Report issued in GB Application No. GB 1504850.7 dated Dec. 2, 2015.

*Primary Examiner* — Nissa M Westerberg
(74) *Attorney, Agent, or Firm* — Troutman Pepper Hamilton Sanders LLP; Ryan A. Schneider; Chris N. Davis

(57) ABSTRACT

The present invention provides an epilatory composition comprising an admixture of a hydrocarbon resin material and a mineral oil in weight ratio of 1.3:1 to 2.8:1, and, a polyethylene in the form of a homopolymer. An advantage of the compositions of the present invention is that they can be heated to the correct temperature of use, and/or to the correct viscosity, in an advantageous time.

20 Claims, No Drawings

EPILATORY COMPOSITIONS

CROSS-REFERENCE TO RELATED APPLICATIONS

This application is a continuation of U.S. patent application Ser. No. 15/558,764, filed 15 Sep. 2017, which is a National Stage Entry of PCT Application No. PCT/GB2016/050793, filed 22 Mar. 2016, which claims priority to GB Application No. GB 1504850.7, filed 23 Mar. 2015, the disclosure of each of which are herein incorporated by reference in their entirety.

BACKGROUND

The present invention relates to an epilatory composition and its use.

BRIEF SUMMARY OF INVENTION

In one aspect, the invention is directed to an epilatory composition comprising a hydrocarbon resin; a mineral oil; and a polyethylene in the form of a homopolymer, wherein the hydrocarbon resin and the mineral oil are present in the composition in a weight ratio in the range of from 1.3:1 to 2.8:1.

In another aspect, the invention is directed to an epilatory composition comprising 63-65 wt % of a hydrocarbon resin; 33-35 wt % of a mineral oil; and 1-2 wt % of a polyethylene in the form of a linear homopolymer.

In another aspect, the invention is directed to an epilatory composition comprising 60-68 wt % of a hydrocarbon resin; 30-35 wt % of a mineral oil; and 0.5-5 wt % of a polyethylene in the form of a linear homopolymer.

In another aspect, the invention is directed to an epilatory composition comprising: 63-66 wt % of a hydrogenated styrene/methyl styrene/indene copolymer; 31-33 wt % of a mineral oil; and 0.75-1.5 wt % of a polyethylene in the form of a linear homopolymer.

In another aspect, the invention is directed to an epilatory composition comprising: 63-66 wt % of a hydrogenated styrene/methyl styrene/indene copolymer; 32-34 wt % of a mineral oil; and 0.75-1.5 wt % of a polyethylene in the form of a linear homopolymer.

In another aspect, the invention is directed to an epilatory composition comprising: 63-66 wt % of a hydrogenated styrene/methyl styrene/indene copolymer; 31-33 wt % of a mineral oil; and 0.8-1.2 wt % of a polyethylene in the form of a linear homopolymer.

Epilatory compositions formed of viscoelastic materials are well known. The viscoelastic materials may in certain embodiments be rosin-based. In other embodiments they may be sugar-based. A tackifier, such as colophony, may be included to make them sticky.

In some products the epilatory compositions may be supplied in devices. The composition is applied from the device onto a user in a controlled manner. In order to do this the device is itself heated in order to soften the composition to allow for efficient application to a user. However, existing waxes can take up to 30 mins before a sufficient amount of the composition has been softened.

In accordance with a first aspect of the present invention there is provided an epilatory composition comprising an admixture of a hydrocarbon resin material and a mineral oil in weight ratio of 1.3:1 to 2.8:1, and a polyethylene in the form of a homopolymer.

Preferably the ratio of hydrocarbon resin to mineral oil is 1.8:1 to 2.1:1. More preferably the ratio is 2:1 to 2.05:1.

Preferably, however, the hydrocarbon resin is selected from poly(methylstyrene-co-indene) or hydrogenated polycyclopentadiene resin. A preferred hydrocarbon resin is hydrogenated polycyclopentadiene resin.

Preferably the epilatory composition comprises from 55-70% wt/wt of hydrocarbon resin material, preferably from 60-68% wt/wt, more preferably 64-66% wt/wt.

DETAILED DESCRIPTION OF INVENTION

The epilatory composition can comprise an oil selected from the group consisting of mineral oils, argan oils and castor oils. A preferred mineral oil is paraffin oil.

Typically, the composition comprises 25-40% wt/wt of the mineral oil. More typically the amount is 30-35% wt/wt. More typically, the amount is 32-34% wt/wt.

The addition of a polyethylene in the form of a homopolymer to an epilatory composition with a resin mix substantially improves the hair removal efficacy of the composition when compared to other polymers known in the art, for example polyisobutane or $C_{1-4}$ polyalkylene.

Preferably the polyethylene has a molecular weight from 100 to 1000, preferably from 250 to 800 more preferably from 300 to 600 unified mass units, most preferably 400-450 units. This gives the advantage of ease of incorporation of the polyethylene into the hydrophobic particles of the invention by melting and blending. Polyethylene suitable for use in compositions of the invention is a linear or non-branched polymer with the structure $CH_3CH_2(CH_2CH_2)_nCH_2CH_3$, where n is a mean number from 8 to 15, preferably 12-14. Preferably at least 90% by weight of the polyethylene is linear or non-branched. A particularly preferred polyethylene is that sold under the registered trade name Performalene. Other suitable polymers include polybutene grades, ethylene and vinyl acetate, goovean fibre viscose, however performalene is preferred.

The polyethylene is typically present in an amount in the range 0.1% to 5% by weight of the composition. Preferably, 0.5% to 4.0%, more preferably 0.5% to 3.0% by weight of the composition. However, a particularly preferred amount is in the range 0.75% to 1.5%, such as around 1.0% by weight of the composition.

The matrix material is suitably a gel-like material with adhesive properties.

The epilatory composition may suitably comprise other components, which may include one or more of a fragrance, an essential oil, a colorant or an anti-oxidant.

In a preferred embodiment there is provided an epilatory composition comprising:
a. 55-70 wt % of a hydrocarbon resin;
b. 25-40 wt % of a mineral oil; and
c. 0.1-5 wt % of a polyethylene in the form of a linear homopolymer.

In a preferred embodiment the composition comprises
a. 64-66 wt % of a hydrocarbon resin;
b. 31-33 wt % of a mineral oil; and
c. 0.8-1.2 wt % of a polyethylene in the form of a linear homopolymer.

In a preferred embodiment the composition comprises
a. 63-65 wt % of a hydrocarbon resin;
b. 33-35 wt % of a mineral oil; and
c. 1-2 wt % of a polyethylene in the form of a linear homopolymer.

In a more preferred embodiment the composition consists essentially of
a. 60-68 wt % of a hydrocarbon resin;
b. 30-35 wt % of a mineral oil; and
c. 0.5-5 wt % of a polyethylene in the form of a linear homopolymer.

In a preferred embodiment the composition consists essentially of
a. 64-66 wt % of a hydrocarbon resin;
b. 31-33 wt % of a mineral oil; and
c. 0.8-1.2 wt % of a polyethylene in the form of a linear homopolymer.

In an alternative embodiment the composition consists essentially of
a. 63-65 wt % of a hydrocarbon resin;
b. 33-35 wt % of a mineral oil; and
c. 1.5-2.0 wt % of a polyethylene in the form of a linear homopolymer.

In a yet further alternative embodiment the composition consists of
a. 64-66% of a hydrogenated polycyclopentadiene resin;
b. 31-35% of a paraffin oil;
c. 0.8-1.2% of polyethylene in the form of a linear homopolymer;
d. about 0.1% of Shea butter;
e. about 0.3% titanium dioxide;
f. about 0.3% fragrance; and
g. about 0.014% dye.

Suitably the epilatory composition is such that its elastic modulus exceeds its viscous modulus at all frequencies up to 0.1 rad/s at 50° C.

Preferably the elastic modulus of the epilatory composition exceeds its viscous modulus at all frequencies up to 1 rad/s at 50° C., more preferably at all frequencies up to 2 rad/s at 50° C.

Preferably at certain higher frequencies (representative of the rapid removal of the epilatory composition from the user's skin), the elastic modulus also exceeds the viscous modulus, at temperatures within the temperature range 20-50° C.

Preferably the elastic modulus exceeds the viscous modulus (when measured at 35° C.) at a frequency of at least 10,000 rad/s, more preferably at a frequency at least 5,000 rad/s.

Thus, preferably the epilatory composition is such that, at ambient temperatures, at low frequencies of applied stress the elastic modulus exceeds the viscous modulus; at high frequencies of applied stress the elastic modulus exceeds the viscous modulus; and at moderate frequencies, in between, the viscous modulus exceeds the elastic modulus. The epilatory composition in transit and storage corresponds to the low frequency condition, and the non-viscous nature of the composition aids shape stability in storage and transit; the application of the epilatory composition to the skin corresponds to the moderate frequency condition, and the viscous nature of the composition aids application and good contact with hair and skin; and pulling the epilatory composition sharply from the skin corresponds to the high frequency condition, the non-viscous, glassy nature of the composition aiding effective hair removal. The transition between the low frequency condition and the moderate frequency condition is known as the gel point. The transition between the moderate frequency condition and the high strain rate condition is known as the glass transition.

The elastic modulus G' (sometimes known as the storage modulus) corresponds to the energy which can be stored and released by a bulk material. The viscous modulus G" (sometimes known as the loss modulus) corresponds to the energy dissipated by a bulk material due to friction between its macromolecules when it is deformed.

$$G' = \frac{\sigma_o \cos \delta}{\gamma_o}$$

$$G'' = \frac{\sigma_o \sin \delta}{\gamma_o}$$

wherein $\sigma_o$ is the stress amplitude, $\gamma_o$ is the strain amplitude and $\delta$ is the out-of-phase coefficient.

The measurements quoted later are based on studies carried out into the rheology of the viscoelastic compositions in order to obtain a better understanding of their adhesive behaviour and their suitability as epilatory materials. These studies involved subjecting the materials to dynamic investigations in which a sinusoidal strain at defined frequencies was applied to the materials and the resulting output force was measured. In these studies a stress control rheometer was used, the SR rheometer commercially available from the company Rheometrics, using parallel plate geometry of 25 mm in diameter. The output force was found to include an in-phase elastic component G' and an out-of-phase viscous component G". The output force can be expressed as follows.

$$\sigma = \sigma_o \sin(t\omega + \delta) = \sigma_o \cos\delta \sin t\omega + \sigma_o \cos\delta \cos t\omega$$

where $\omega$ is the test frequency and t is the time.

Within the linear stress-strain domain of the material G' is desirably lower than G" at moderate frequency oscillation in order to prevent the material cracking and to ensure that the material has strong adhesion at the material/hair interface. The values of G' and G" at moderate frequency oscillation are a measure of how readily the material wets the hairs. Moderate frequency oscillation is a long time process and corresponds to the time when the material is being applied to the skin. The lower values of G' and G" at this moderate frequency, the better the material wets the hairs. Thus the hairs become well embedded in the material in a very short time (ie the time needed for spreading the material on the skin). However G' should be higher than G" at high frequency oscillation (which mimics the action of the user in rapidly pulling the strip from the body) in order to remove hairs efficiently. Also, at low frequency oscillation, or no oscillation, G' is preferably higher than G", in accordance with this invention, in order to obtain the benefit of enhanced stability, even when warm.

The definitions given herein refer to stresses applied to the material within its linear stress-strain domain, which may typically be up to a few thousand Pa.

By ensuring that the epilatory composition satisfies the above parameters, it can be readily applied to the skin at body temperature, yet it is very efficient at removing hairs from the skin and, surprisingly, the user experiences less pain.

Whilst we are not bound by any theory, we believe that the composition of the present invention has improved heating efficacy as a result of the combination of materials lowering the heat of fusion. The intermolecular forces between the resin are strong and as result the energy required to break these forces and "melt" the resin is high—the combination of ingredients interrupts the intermolecular forces between the resin molecules and then lowers the heat of fusion and thus lowers the melting point significantly.

If wished the epilatory composition of the present invention may be provided in a container, from which the user removes it using, for example, a spatula or an applicator fitted to the container, and applies it to the skin. A fabric can then be used to pull the applied material in one piece from the skin.

Example embodiments of the present invention will now be further described.

Example 1

| Standard Name | Function | Percentage |
| --- | --- | --- |
| Petroleum Hydrocarbon Resin | Epilatory Agent | 65.85 |
| Thick Mineral Oil | Solvent | 32.43 |
| Polyethylene | Rheology Modifier | 1.00 |
| Shea Butter | Cosmetic Active | 0.10 |
| Fragrance | Fragrance | 0.62 |
| | | 100.00 |

The compositions of the present application can be made in the following way:

The thick mineral oil is heated with stirring to approximately 100° C., the resin is then added very gradually with continuous stirring. Each batch of resin pellets are allowed to fully melt before adding more. The stirring speed can be increased. Once all the resin has melted, the polyethylene and shea butter are added. Finally the premix is added with stirring until fully mixed in. The resulting composition is allowed to cool.

Example 2

| Standard Name | Function | Percentage |
| --- | --- | --- |
| Petroleum Hydrocarbon Resin | Epilatory Agent | 63.84 |
| Thick Mineral Oil | Solvent | 34.41 |
| Polyethylene | Rheology Modifier | 1.75 |
| | | 100.00 |

Example 2 can be made in a similar way to Example 1 but without including the fragrance and shea butter.

An advantage of the present invention is that there is provided an epilatory composition having improved heating time allowing the composition to reach the correct temperature of use more quickly than current compositions.

Further modifications and improvements can be made without departing from the scope of the invention described herein.

What is claimed is:

1. An epilatory composition comprising:
   63-66 wt % of a hydrogenated styrene/methyl styrene/indene copolymer;
   31-33 wt % of a mineral oil; and
   0.75-1.5 wt % of a polyethylene in the form of a linear homopolymer.

2. An epilatory composition comprising:
   63-66 wt % of a hydrogenated styrene/methyl styrene/indene copolymer;
   32-34 wt % of a mineral oil; and
   0.75-1.5 wt % of a polyethylene in the form of a linear homopolymer.

3. An epilatory composition comprising:
   63-66 wt % of a hydrogenated styrene/methyl styrene/indene copolymer;
   31-33 wt % of a mineral oil; and
   0.8-1.2 wt % of a polyethylene in the form of a linear homopolymer.

4. The epilatory composition as claimed in claim 1, wherein the polyethylene has a molecular weight from 100 to 1000 unified mass units.

5. The epilatory composition as claimed in claim 2, wherein the polyethylene has a molecular weight from 100 to 1000 unified mass units.

6. The epilatory composition as claimed in claim 3, wherein the polyethylene has a molecular weight from 100 to 1000 unified mass units.

7. The epilatory composition as claimed in claim 1, wherein the hydrogenated styrene/methyl styrene/indene copolymer is present in an amount of about 63% to about 65% by weight of the composition.

8. The epilatory composition as claimed in claim 2, wherein the hydrogenated styrene/methyl styrene/indene copolymer is present in an amount of about 63% to about 65% by weight of the composition.

9. The epilatory composition as claimed in claim 3, wherein the hydrogenated styrene/methyl styrene/indene copolymer is present in an amount of about 63% to about 65% by weight of the composition.

10. The epilatory composition as claimed in claim 1, wherein the mineral oil is present in an amount of about 32% to about 33% by weight of the composition.

11. The epilatory composition as claimed in claim 2, wherein the mineral oil is present in an amount of about 32% to about 33% by weight of the composition.

12. The epilatory composition as claimed in claim 3, wherein the mineral oil is present in an amount of about 32% to about 33% by weight of the composition.

13. The epilatory composition as claimed in claim 1, wherein the mineral oil is selected from the group consisting of mineral oils, argan oils and castor oils.

14. The epilatory composition as claimed in claim 2, wherein the mineral oil is selected from the group consisting of mineral oils, argan oils and castor oils.

15. The epilatory composition as claimed in claim 3, wherein the mineral oil is selected from the group consisting of mineral oils, argan oils and castor oils.

16. The epilatory composition as claimed in claim 1, wherein the mineral oil is a paraffin oil.

17. The epilatory composition as claimed in claim 2, wherein the mineral oil is a paraffin oil.

18. The epilatory composition as claimed in claim 3, wherein the mineral oil is a paraffin oil.

19. The epilatory composition as claimed in claim 1, wherein the polyethylene is present in an amount of about 1.0% by weight of the composition.

20. The epilatory composition as claimed in claim 2, wherein the polyethylene is present in an amount of about 1.0% by weight of the composition.

* * * * *